(12) United States Patent
Hsiao et al.

(10) Patent No.: US 11,981,846 B2
(45) Date of Patent: May 14, 2024

(54) NANOCOMPOSITE AND USES THEREOF

(71) Applicant: Academia Sinica, Taipei (TW)

(72) Inventors: Michael Hsiao, Taipei (TW); Ming-Hsien Chan, Taipei (TW); Subbiramaniyan Kubendhiran, Taipei (TW); Ming-Che Hsieh, Taipei (TW); Zhen Bao, Changzhou (CN); An-Bang Wang, Taipei (TW); Ru-Shi Liu, Taipei (TW)

(73) Assignee: ACADEMIA SINICA, Taipei (TW)

( * ) Notice: Subject to any disclaimer, the term of this patent is extended or adjusted under 35 U.S.C. 154(b) by 213 days.

(21) Appl. No.: 17/611,896

(22) PCT Filed: Jul. 29, 2020

(86) PCT No.: PCT/US2020/043970
§ 371 (c)(1),
(2) Date: Nov. 16, 2021

(87) PCT Pub. No.: WO2021/021866
PCT Pub. Date: Feb. 4, 2021

(65) Prior Publication Data
US 2022/0220370 A1 Jul. 14, 2022

Related U.S. Application Data

(60) Provisional application No. 62/881,384, filed on Aug. 1, 2019.

(51) Int. Cl.
*C09K 11/02* (2006.01)
*C09K 11/56* (2006.01)
(Continued)

(52) U.S. Cl.
CPC .......... *C09K 11/025* (2013.01); *C09K 11/565* (2013.01); *C09K 11/70* (2013.01);
(Continued)

(58) Field of Classification Search
CPC ... C09K 11/025; C09K 11/565; C09K 11/562; C09K 11/70; C09K 11/7773; C09K 11/883
See application file for complete search history.

(56) References Cited

U.S. PATENT DOCUMENTS

| | | | |
|---|---|---|---|
| 2005/0208543 A1* | 9/2005 | Vann | B82Y 5/00 435/6.12 |
| 2015/0241349 A1* | 8/2015 | Cohen | C09K 11/7773 250/459.1 |
| 2017/0211756 A1* | 7/2017 | Koole | F21K 9/64 |

OTHER PUBLICATIONS

Chan. Near-Infrared-Activated Fluorescence Resonance Energy TransferBased Nanocomposite to Sense MMP2-Overexpressing Oral Cancer Cells. ACS Omega 2018, 3, 1627-1634 (Year: 2018).*

* cited by examiner

*Primary Examiner* — Matthew E. Hoban
(74) *Attorney, Agent, or Firm* — NZ Carr Law Office, PLLC (57) ABSTRACT

Disclosed herein is a nanocomposite comprising a core-shell nanoparticle and a core-shell quantum dot. The core-shell nanoparticle comprises a phosphor core, a shell layer, and a cleavable peptide. The core-shell quantum dot comprises a center core, an intermediate layer, an outer layer, a silica layer, and an arginylglycylaspartic acid (RGD) peptide. The core-shell nanoparticle and the core-shell quantum dot are linked to each other via forming a peptide bond between the cleavable peptide and the RGD peptide. Also disclosed are the uses of the nanocomposite in making a diagnosis of tumors.

10 Claims, 10 Drawing Sheets

(51) Int. Cl.
 *C09K 11/70* (2006.01)
 *C09K 11/77* (2006.01)
 *C09K 11/88* (2006.01)
 *G01N 33/58* (2006.01)
 *B82Y 20/00* (2011.01)
 *B82Y 40/00* (2011.01)
(52) U.S. Cl.
 CPC ........ *C09K 11/7773* (2013.01); *C09K 11/883* (2013.01); *G01N 33/587* (2013.01); *G01N 33/588* (2013.01); *B82Y 20/00* (2013.01); *B82Y 40/00* (2013.01); *G01N 2458/00* (2013.01)

NANOCOMPOSITE AND USES THEREOF

CROSS-REFERENCES TO RELATED APPLICATIONS

This application is a U.S. National Stage Filing under 35 U.S.C. 371 from International Patent Application Serial No. PCT/US2020/043970, entitled "NANOCOMPOSITE AND USES THEREOF," filed on Jul. 29, 2020, and published on Feb. 4, 2020, which claims the priority and the benefit of U.S. Provisional Patent Application No. 62/881,384, filed Aug. 1, 2019, the disclosure of which are incorporated by reference herein in their entireties.

BACKGROUND OF THE INVENTION

1. Field of the Invention

The present disclosure in general relates to the field of tumor diagnosis. More particularly, the present disclosure relates to a novel nanocomposite and uses thereof in the diagnosis of tumors.

2. Description of Related Art

Cancer is a group of diseases caused by abnormal cell growth. According to the report of World Health Organization (WHO), cancer is the second leading cause of death globally that is responsible for an estimated 9.6 million deaths in 2018. Common cancers include lung cancer, colorectal cancer, stomach cancer (also known as gastric cancer), liver cancer, and breast cancer, which collectively lead to 4.8 million deaths in 2018. Early diagnosis is crucial to improve the survival rates of cancer patients. Compared with late-stage cancers, early-stage cancers are more responsive to anti-tumor treatments.

The most common approaches to diagnose cancers include imaging tests (e.g., computerized tomography (CT) scan, bone scan, magnetic resonance imaging (MRI), positron emission tomography (PET) scan, ultrasound examination, and X-ray examination), laboratory tests (e.g., urine and blood tests for evaluating the expression of specific tumor markers), and biopsies (i.e., the examination of tissue sample under a microscope by a pathologist). However, none of these approaches provides a satisfactory effect due to various limitations, such as high cost, low accuracy, low sensitivity, time and/or labor intensive, and undesired side effect (e.g., tissue damage, pain, or infection).

In view of the foregoing, there exists in the related art a need for a novel method for making an early diagnosis of cancers in a safer and accurate manner so as to improve the life quality and life span of cancer patients.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

As embodied and broadly described herein, one aspect of the disclosure is directed to a nanocomposite, which comprises a core-shell nanoparticle, and a core-shell quantum dot coupled to the core-shell nanoparticle. According to embodiments of the present disclosure, the core-shell nanoparticle comprises a phosphor core, a shell layer encapsulating the phosphor core, and a cleavable peptide coupled to the shell layer; and the core-shell quantum dot comprises a center core, an intermediate layer encapsulating the center core, an outer layer encapsulating the intermediate layer, a silica layer encapsulating the outer layer, and an arginylglycylaspartic acid (RGD) peptide coupled to the silica layer. In structure, the core-shell nanoparticle is linked with the core-shell quantum dot via forming a peptide bond between the cleavable peptide and the RGD peptide.

According to some embodiments of the present disclosure, the phosphor core is made of a first phosphor material doped with one or more emitter ions, and the shell layer is made of a second phosphor material doped with one or more absorber ions. In general, the first and second phosphor materials are independently selected from the group consisting of, sodium yttrium fluoride, lanthanum fluoride, lanthanum oxysulfide, yttrium oxysulfide, yttrium fluoride, yttrium gallate, yttrium aluminum garnet, gadolinium fluoride, barium yttrium fluoride, and gadolinium oxysulfide. The emitter ion and absorber ion are independently selected from the group consisting of, erbium (Er), ytterbium (Yb), thulium (Tm), holmium (Ho), neodymium (Nd), and praseodymium (Pr). According to some working embodiments, each of the first and second phosphor materials is sodium yttrium fluoride. Preferably, the first phosphor material is doped with Yb and Er, and the second phosphor material is doped with Yb and Nd. In these embodiments, the core-shell nanoparticle has a polygonal shape, in which each side of the polygon has an average length of about 20-35 nm; preferably, about 25-30 nm; more preferably, about 25-27 nm.

Depending on desired purposes, the cleavable peptide may be a peptide cleavable by matrix metallopeptidase (MMP), cathepsin, plasminogen activator (PA) or other tumor-associated peptidases. According to one specific example, the cleavable peptide is cleavable by MMP-2.

According to certain embodiments of the present disclosure, the center core is made of indium phosphide (InP), cadmium selenide (CdSe), cadmium selenide sulphide (CdSeS), zinc selenide (ZnSe), zinc cadmium selenide (ZnCdSe), or cadmium telluride (CdTe); the intermediate layer is made of cadmium sulphide (CdS), cadmium zinc sulphide (CdZnS), or zinc selenide sulphide (ZnSeS); and the outer layer is made of zinc sulphide (ZnS). According to one working example, the center core is made of InP, and the intermediate layer is made of ZnSeS. In this example, the core-shell quantum dot has a spherical shape, and an average diameter about 1-20 nm; preferably, about 5-20 nm; more preferably, about 7-15 nm.

Another aspect of the present disclosure pertains to the use of the present nanocomposite in making a diagnosis of a tumor from a biological sample of a subject. The method comprises,
(a) contacting the biological sample with an effective amount of the present nanocomposite;
(b) irradiating the product of the step (a) with a light beam;
(c) determining the wavelength emitted from the product of the step (b); and
(d) making the diagnosis that the subject has the tumor if the determined wavelength of the step (c) differs from that of a control sample.

According to certain working examples of the present disclosure, the first phosphor material of the core-shell nanoparticle is made of sodium yttrium fluoride doped with Yb and Er; the second phosphor material of the core-shell nanoparticle is made of sodium yttrium fluoride doped with Yb and Nd; the center core of the core-shell quantum dot is made of InP; and the intermediate layer of the core-shell quantum dot is made of ZnSeS.

According the certain embodiments of the present disclosure, the light beam has a wavelength of about 750-850 nm, and a wavelength of about 500-570 nm emitted from the biological sample indicates that the subject has the tumor. Preferably, the light beam has a wavelength of about 808 nm, and a wavelength of about 520-540 nm emitted from the biological sample indicates that the subject has the tumor.

The tumor of the present disclosure may be any tumor having a tumor-associated peptidase overexpressed therein/thereon, for example, MMP, cathepsin, or PA. In certain embodiments, the tumor overexpresses MMP-2, and is selected from the group consisting of melanoma, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, and head and neck squamous cell carcinoma.

The subject is a mammal; preferably, a human.

Many of the attendant features and advantages of the present disclosure will becomes better understood with reference to the following detailed description considered in connection with the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present description will be better understood from the following detailed description read in light of the accompanying drawings, where:

FIG. 7 is the data depicting the effect of RGD peptide on cellular uptake of the present nanocomposite according to Example 2 of the present disclosure. UCNP-p@InP: $NaYF_4$:Yb/Er@$NaYF_4$:Yb/Nd coupled with InP/ZnSeS/ZnS quantum dot, in which the $NaYF_4$:Yb/Er@$NaYF_4$:Yb/Nd has an MMP-2-cleavable peptide coupled thereon, and the InP/ZnSeS/ZnS quantum dot is coated with a silica shell; UCNP-p@InP-cRGD: $NaYF_4$:Yb/Er@$NaYF_4$:Yb/Nd coupled with InP/ZnSeS/ZnS quantum dot, in which the $NaYF_4$:Yb/Er@$NaYF_4$:Yb/Nd has an MMP-2-cleavable peptide coupled thereon, and the InP/ZnSeS/ZnS quantum dot is coated with a silica shell and has a RGD peptide coupled thereon.

FIG. 9 is the data of spectrum images according to Example 2 of the present disclosure. MMP2 expression constructed in an MMP2-deficient cell lines Ca922 and HSC4. Composite nanoparticles combine two or more substances in a single particle. In addition to combining multiple functions, new properties of upconverting nanoparticles as a specific biosensor can also be generated.

In accordance with common practice, the various described features/elements are not drawn to scale but instead are drawn to best illustrate specific features/elements relevant to the present invention. Also, like reference numerals and designations in the various drawings are used to indicate like elements/parts.

DETAILED DESCRIPTION OF THE INVENTION

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

I. Definition

For convenience, certain terms employed in the specification, examples and appended claims are collected here.

Unless otherwise defined herein, scientific and technical terminologies employed in the present disclosure shall have the meanings that are commonly understood and used by one of ordinary skill in the art. Also, unless otherwise required by context, it will be understood that singular terms shall include plural forms of the same and plural terms shall include the singular. Specifically, as used herein and in the claims, the singular forms "a" and "an" include the plural reference unless the context clearly indicates otherwise. Also, as used herein and in the claims, the terms "at least one" and "one or more" have the same meaning and include one, two, three, or more.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about". Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

As used herein, the term "phosphor" refers to any substance that absorbs light at one wavelength and emits light at another wavelength, regardless of the delay between absorption and emission, and regardless of the wavelengths involved.

The term "nanoparticle" as used herein refers to any particle that is on the order of $10^{-9}$ meter, or one billionth of a meter. Specifically, the term "nanoparticle" refers to any particle having a diameter of less than 1,000 nanometer (nm). In various embodiments, the nanoparticle has a characteristic size (e.g., diameter or edge side) less than about 1,000 nm, 800 nm, or 500 nm; preferably less than about 400 nm, 300 nm, or 200 nm; more preferably about 100 nm or less, about 50 nm or less, or about 30 or 20 nm or less. Nanoparticles can comprise a core, a core and a shell (as in core-shell nanoparticles), or a core and multiple shells (as in core-multi-shell particles).

The term "quantum dot" (QD) as used herein is understood to apply to its conventional meaning of a material domain that is small enough to induce quantum-size effects that exhibit the electronic, optical, or opto-electronic characteristics of an electron gas. Specifically, the term "quantum dot" (QD) refers to a semiconductor nanocrystal that includes a core of at least one of a Group II-VI semiconductor material, a Group III-V semiconductor material, a Group IV semiconductor material, or a combination thereof. Examples of quantum dots (QDs) that can be used in the invention include nanocrystals of CdSe, CdSeS, CdZnS, ZnCdSe, ZnS, ZnSe, ZnSeS, ZnTe, CdS, CdTe, GaN, GaP, GaAs, GaSb, InP, INAs, InSb, AlS, AlP, AlAs, AlSb, PbS, PbSe, an GeSi, ternary or quaternary mixtures thereof.

The term "dope" or "doped" refers to a very small amount (e.g., trace amount) of an ion (e.g., Er, Yb, Tm, Ho, Nd, or Pr) added to modify the electronic or physical properties of a substance (e.g., the phosphor material of the present disclosure) or to give it new properties.

The term "encapsulate" refers to the process of encompassing, encasing, or otherwise associating two or more materials such that the encapsulated material is immobilized within or onto the encapsulating material.

The term "subject" refers to a mammal including the human species that is suitable to be diagnosed by methods of the present invention. The term "subject" is intended to refer to both the male and female gender unless one gender is specifically indicated.

The term "healthy subject" refers to a subject that does not have a disease (e.g., a cancer). For example, a healthy subject has not been diagnosed as having a disease and is not presenting with two or more (e.g., two, three, four or five) symptoms associated with the disease.

The term "biological sample" refers to any sample including tissue samples (such as tissue sections and needle biopsies of a tissue), or cell samples (e.g., cytological smears (such as Pap or blood smears) or samples of cells obtained by microdissection). Other examples of biological samples include blood, serum, urine, semen, fecal matter, cerebrospinal fluid, interstitial fluid, mucous, tears, sweat, pus, biopsied tissue (e.g., obtained by a surgical biopsy or needle biopsy), nipple aspirates, milk, vaginal fluid, saliva, swabs (such as buccal swabs), or any material containing biomolecules that is derived from a first biological sample.

As used herein, the term "derived," when referring to a biological sample, indicates that the sample was obtained from the stated source at some point in time. For example, a biological sample derived from an individual can represent a primary biological sample obtained directly from the individual (i.e., unmodified), or can be modified, e.g., by introduction of a recombinant vector, by culturing under particular conditions, or immortalization.

II. Description of the Invention

The objective of the present disclosure aims at providing a nanocomposite, which comprises a core-shell nanoparticle and at least one core-shell quantum dot coupled with the core-shell nanoparticle via forming a peptide bond therebetween. The present nanocomposite is characterized in that the cleavage of the peptide bond results in the alteration of the optical properties of the nanocomposite. Specifically, in the case when the core-shell nanoparticle is coupled with the core-shell quantum dot, it has an excitation wavelength of 808 nm, and an emission wavelength of 650-750 nm. When the peptide bond is cleaved (e.g., by the action of an enzyme) that results in the release of the core-shell quantum dot from the core-shell nanoparticle, then the exciting wavelength of the cleaved nanocomposite would be blue-shift from 808 nm to a green emitted light ranging between 520-540 nm. Accordingly, the present nanocomposite is useful in detecting desired cells (e.g., cancer cells) having specific enzyme (e.g., MMP-2) overexpressed therein/thereon.

Figure 1:
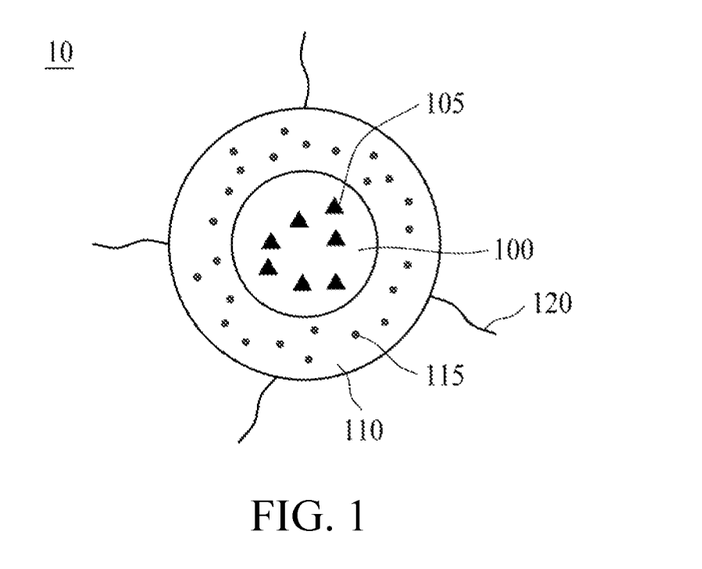
FIG. 1 is a schematic diagram depicting the core-shell nanoparticle of the present nanocomposite.
Figure 2:
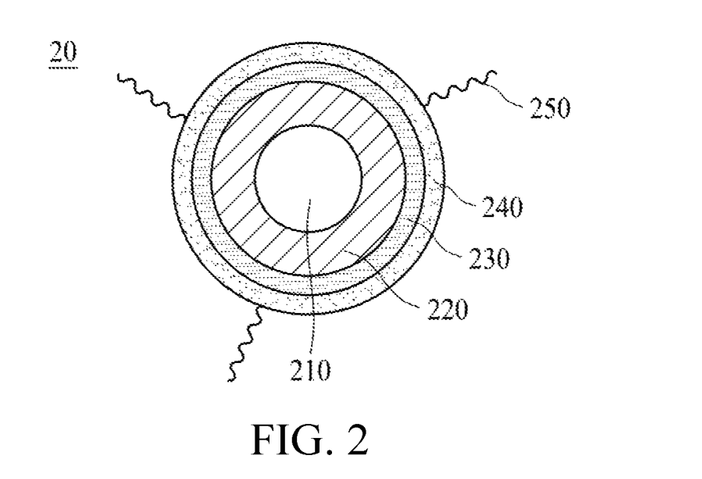
FIG. 2 is a schematic diagram depicting the core-shell quantum dot of the present nanocomposite.

The first aspect of the present disclosure is directed to a nanocomposite, which comprises a core-shell nanoparticle and at least one core-shell quantum dot coupled therewith. Exemplary structures of the core-shell nanoparticle and the core-shell quantum dot are schematically illustrated in FIGS. 1 and 2, respectively. As depicted in FIG. 1, the core-shell nanoparticle 10 comprises a phosphor core 100, a shell layer 110, and a cleavable peptide 120. In structure, the phosphor core 100 is encapsulated by the shell layer 110, and the cleavable peptide 120 is coupled to the outer surface of the shell layer 110.

Regarding the material forming the phosphor core 100 and the shell layer 110, it may be any phosphor material that absorbs and emits lights at different wavelengths; exemplary phosphor materials suitable for forming the phosphor core 100 and the shell layer 110 include, but are not limited to, sodium yttrium fluoride, lanthanum fluoride, lanthanum oxysulfide, yttrium oxysulfide, yttrium fluoride, yttrium gallate, yttrium aluminum garnet, gadolinium fluoride, barium yttrium fluoride, and gadolinium oxysulfide.

As exemplified in FIG. 1, the phosphor core 100 and the shell layer 110 respectively have the first plurality of ions 105 and the second plurality of ions 115 doped therein, in which the first and second plurality of ions 105, 115 respectively serve as energy acceptor and energy donor during energy transfer (ET) process. Examples of doping ions commonly used in the production of nanoparticle include, but are not limited to, Er, Yb, Tm, Ho, Nd, and Pr. According to some embodiments of the present disclosure, the phosphor core 100 is made of sodium yttrium fluoride having Yb and Er doped therein, and the shell layer 110 is made of sodium yttrium fluoride having Yb and Nd therein. The thus-produced core-shell nanoparticle is termed as "NaYF$_4$: Yb/Er@NaYF$_4$:Yb/Nd", in which the Nd, Yb and Er ions respectively serve as the energy absorber, intermediator and emitter ions (i.e., an ET process of Nd$^{3+}$→Yb$^{3+}$→Er$^{3+}$).

Depending on desired purposes, the cleavable peptide 120 may be a peptide cleavable by any tumor-associated peptidase, such as, matrix metallopeptidase (MMP; including MMP-1, MMP-2, MMP-3, MMP-7, MMP-8, MMP-9, MMP-10, MMP-11, MMP-12; MMP-13; MMP-14, MMP-15, MMP-16, MMP-17, MMP-18, MMP-19, MMP-20, MMP-21, MMP-23, MMP-24, MMP-25, MMP-26, MMP-27, and MMP-28), cathepsin (including cathepsin A, B, C, D, E, F, G, H, L, K, O, S, V, and W), plasminogen activator (PA). For example, when the peptide is an MMP-2-cleavable peptide, then the nanocomposite may be used to detect a tumor having MMP-2 overexpressed therein/thereon, e.g., a lung tumor, a pancreatic tumor, a breast tumor, a testis tumor, or a head and neck tumor. Alternatively, in the case when the peptide is a cathepsin B-cleavable peptide, then the nanocomposite may be used to detect a tumor having cathepsin B overexpressed therein/thereon, e.g., a brain tumor, a lung tumor, a prostate tumor, a breast tumor, or a colorectal tumor. According to some working examples of the present disclosure, the cleavable peptide 120 is an MMP-2-cleavable peptide. In one specific example, the cleavable peptide 120 comprises the amino acid sequence of "SGAVRWLLTA".

Reference is made to FIG. 2, which is an exemplary schematic structure of the core-shell quantum dot of the present nanocomposite. The core-shell quantum dot 20 comprises a center core 210, an intermediate layer 220, an outer layer 230, a silica layer 240, and a RGD peptide 250. In structure, the center core 210 is encapsulated, in sequence, by the intermediate layer 220, the outer layer 230, and the silica layer 240; then, RGD peptide 250 is coupled to the outer surface of the silica layer 240.

The core-shell quantum dot 20 may be essentially made of any desired material, for example, a Group II-VI semiconductor, a Group III-V semiconductor, or a combination thereof. According to some embodiments, the center core 210 is made of indium phosphide (InP), cadmium selenide (CdSe), cadmium selenide sulphide (CdSeS), zinc selenide (ZnSe), zinc cadmium selenide (ZnCdSe), or cadmium telluride (CdTe); the intermediate layer 220 is made of cadmium sulphide (CdS), cadmium zinc sulphide (CdZnS), or zinc selenide sulphide (ZnSeS); and the outer layer 230 is made of zinc sulphide (ZnS). According to some preferred embodiments, the center core 210 is made of InP, and the intermediate layer 220 is made of ZnSeS. In these embodiments, the thus-produced core-shell quantum dot is termed as "InP/ZnSeS/ZnS@S". The structure of the ZnSeS shell is known by a skilled artisan that may be alternatively expressed as the formula of ZnSe$_x$S$_{1-x}$, where 0<X<1; preferably, 0.25≤X≤0.75; more preferably, X is about 0.5. The percentage of Se gradually increases from the outer surface of the intermediate layer 220 (i.e., the surface contacting with the outer layer 230) to the inner surface of the intermediate layer 220 (i.e., the surface contacting with the center core 210); while the percentage of S gradually decreases from the outer surface of the intermediate layer 220 to the inner surface of the intermediate layer 220.

Figure 3:
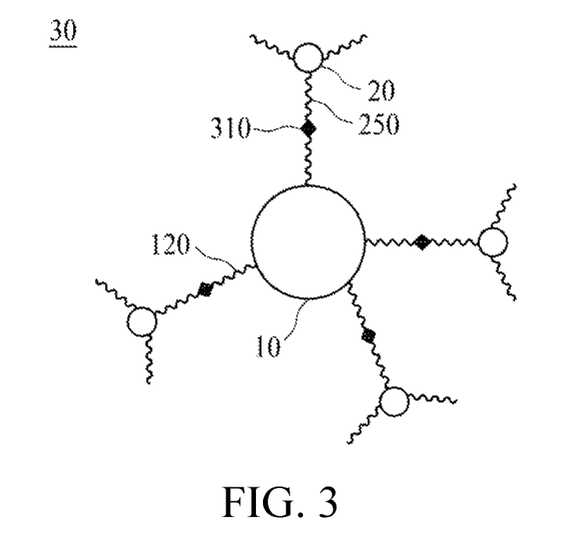
FIG. 3 is a schematic diagram depicting the present nanocomposite, which comprises one core-shell nanoparticle and four core-shell quantum dots coupled therewith.

Reference is now made to FIG. 3, which depicts the coupling of the core-shell nanoparticle 10 and the core-shell quantum dot 20 via forming a peptide bond 310 between the cleavable peptide 120 and the RGD peptide 250. The thus-produced nanocomposite 30 is advantageous in possessing, (1) the RGD peptide 250 coupled therewith, which may effectively mediate or enhance cellular uptake of the nanocomposite 30; and (2) the cleavable peptide 120, in which two particles (i.e., the core-shell nanoparticle 10 and the core-shell quantum dot 20) independently having different optical properties are linked thereby; once the cleavable peptide 120 is cleaved by specific enzyme (e.g., MMP-2), the separation of said two previously linked particles results in alteration of the optical properties (e.g., the emitting wavelength) of the nanocomposite, so that the presence and/or location of specific cells having the specific enzyme expressed/overexpressed therein and/or thereon may be detected.

The number of the core-shell quantum dot coupled with the core-shell nanoparticle may vary with desired purposes. In general, the nanocomposite comprises at least two (e.g., 2, 3, 4, 5, 6, 7, 8, 9, 10, or more) core-shell quantum dots coupled with the core-shell nanoparticle. Preferably, the nanocomposite comprises at least 3 (i.e., 3, 4, 5, 6, 7, or more) core-shell quantum dots coupled with the core-shell nanoparticle.

In various embodiments of the present disclosure, the core-shell nanoparticle and the core-shell quantum dot are independently shaped as a polygon (for example, octahedral shape), a needle, a dumbbell, a rod, a sphere, a pyramid, or a cylinder. According to some specific examples, the core-shell nanoparticle has a polygonal shape, in which each side of the polygon has an average length of about 20-35 nm; and the core-shell quantum dot has a spherical shape, in which the average diameter is about 1-20 nm. According to the preferred embodiments, the core-shell nanoparticle has an average length of about 25-30 nm, and the core-shell quantum dot has an average diameter of about 5-20 nm. In one working example of the present disclosure, the average length of the core-shell nanoparticle is about 25-27 nm, and the average diameter of the core-shell quantum dot is about 7-15 nm.

Also disclosed herein are uses of the nanocomposite in accordance with any embodiment of the present disclosure in the detection of tumor cells in a biological sample or in a subject. The method of making diagnosing a tumor from a biological sample of a subject comprises the steps of, (a) contacting the biological sample with an effective amount of the present nanocomposite;

(b) irradiating the product of the step (a) with a light beam;

(c) determining the wavelength emitted from the product of the step (b); and (d) making the diagnosis that the subject has the tumor if the determined wavelength of the step (c) differs from that of a control sample.

Basically, the biological sample may be any tissue sample or cell sample in accordance with desired purposes. Preferably, the biological sample is a surgical biopsy sample or a needle biopsy sample.

In the step (a), the biological sample is incubated an effective amount of the present nanocomposite for a period of time so that the nanocomposite is uptaken by the cell of the biological sample.

Preferably, after the incubation, the method further comprises a step of removing free nanocomposite, i.e., the nanocomposite without binding to or entering into the cell.

Then, in the step (b), the incubated biological sample is exposed to a light beam so as to excite the nanocomposite in the cell. In general, the light beam has a wavelength of about 750-850 nm; for example, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, or 850 nm. According to preferred embodiments, the light beam has a wavelength of about 780-820 nm. In one specific example of the present disclosure, the light beam has a wavelength of about 808 nm.

After exposing to the light beam, the emitting wavelength from the incubated biological sample is detected and compared with that of the control sample (e.g., a biological sample derived from a healthy subject) as illustrated in the step (c). The emitting wavelengths of the biological sample and the control sample may be detected by any method familiar with the person having ordinary skill in the art, such as microscope (including, optical microscope or fluorescence microscope), spectrometer, or spectrum imaging system.

Next, in the step (d), the diagnosis of tumor is performed based on the comparison result of the step (c). Specifically, as mentioned above, the cleavage of the cleavable peptide alters the optical properties of the nanocomposite. Thus, in the case when the tumor cell overexpresses an enzyme exhibiting cleavage activity on the cleavable peptide, then the nanocomposite in said tumor cell would emit a different wavelength from that of the normal cell (i.e., the cell without overexpressing the enzyme). As could be appreciated, the emitting wavelengths of the biological sample and the control sample vary with the wavelength of the exciting light beam. According to certain embodiments, upon the excitation of a light beam having a wavelength of about 750-850 nm, the un-cleaved nanocomposite in the normal cell would emit a wavelength of about 600-800 nm, while the cleaved nanocomposite in the tumor cell would emit a wavelength of about 500-570 nm. According to some working examples of the present disclosure, the core-shell nanoparticle is $NaYF_4$:Yb/Er@$NaYF_4$:Yb/Nd, and the core-shell quantum dot is InP/ZnSeS/ZnS@S, in which the exposure of 808 nm irradiation triggers the nanocomposites in the normal and tumor cells respectively emit wavelengths of about 650-750 nm and 520-540 nm.

Another aspect of the present disclosure pertains to a method of making a diagnosis of a tumor in a subject by use of the present nanocomposite. The method comprises the steps of, (1) administering to the subject an effective amount of the present nanocomposite;

(2) irradiating the subject of the step (1) with a light beam;

(3) determining the wavelength emitted from the subject of the step (2); and (4) making the diagnosis that the subject has the tumor if the determined wavelength of the step (3) differs from a reference wavelength of a healthy subject.

The method of diagnosing tumors in the subject is similar to that of diagnosing tumors in the biological sample as described above, and hence, detailed description thereof is omitted herein for the sake of brevity.

As could be appreciated, the cleavable peptide of the nanocomposite may vary with the type of tumor detected. For example, for the purpose of diagnosing a pancreatic tumor having MMP-2 overexpressed therein, an MMP-2-cleavable peptide is employed in the nanocomposite to couple the core-shell nanoparticle and the core-shell quantum dot. Alternatively, the nanocomposite comprising a cathepsin B-cleavable peptide is useful in diagnosing a colorectal tumor having cathepsin B overexpressed therein. According to one working example, the cleavable peptide of the nanocomposite is an MMP-2-cleavable peptide, which comprises the amino acid sequence of "SGAVRWLLTA".

Basically, the tumor of the present disclosure may be any of melanoma, leukemia, tongue carcinoma, colorectal carcinoma, esophageal carcinoma, gastric carcinoma, lung cancer, multiple myeloma, bladder cancer, breast cancer, pancreatic cancer, renal cancer, hepatocellular carcinoma, ovarian cancer, prostate cancer, or head and neck squamous cell carcinoma.

The subject is a mammal, for example, a human, a mouse, a rat, a hamster, a guinea pig, a rabbit, a dog, a cat, a cow, a goat, a sheep, a monkey, and a horse. Preferably, the subject is a human.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent. All publications cited herein are hereby incorporated by reference in their entirety.

EXAMPLE

Materials and Methods

Reagents

All chemical materials were obtained from commercial suppliers. These chemicals did not require further purification. The synthetic chemicals of InP QDs included $In(C_2H_3O_2)_3$ (99.99%), $[(CH_3)_3Si]_3P$ (98%), myristic acid (98%), $CH_3(CH_2)_{11}SH$ (≥98%), $[CH_3(CH_2)_{16}COO]_2Zn$ (10%, Zn basis), oleic acid (90%), 1-octadecene (90%), n-trioctylphosphine (90%), selenium powder (99.99%), $(CH_3CO_2)_2Zn$ (99%), and hexane (99.99%). The synthetic chemicals of UCNPs included $Nd(CH_3CO_2)_3 \cdot H_2O$ (99.99%), $Y(CH_3CO_2)_3 \cdot H_2O$ (99.99%), $Yb(CH_3CO_2)_3 \cdot H_2O$ (99.99%), $Er(CH_3CO_2)_3 \cdot H_2O$ (99.99%), sodium hydroxide (NaOH, 98%), and hydrochloric acid (HCl, 37%). The chemicals used for the modification included APTES (98%), IGEPAL® CO-520, tetraethyl orthosilicate (98%), N-(3- dimethylaminopropyl)-N-ethylcarbodiimide hydrochloride (EDC), N-hydroxysuccinimide (NHS), chitosan (mol/wt 50,000-190,000 Da), and Arg-Gly-Asp (≥97%).

Synthesis of InP/ZnSeS/ZnS QD with silica shell coating (InP@S QD)

InP/ZnSeS/ZnS QDs were synthesized using the hot injection method. In total, 0.3 mmol of indium acetate, 1.35 mmol of myristic acid, 0.3 mmol of zinc stearate, and 10 mL of 1-octadecene (ODE) were mixed in a three-necked flask under vacuum. The rotation speed was 450 rpm, and the temperature was increased to 120° C. and maintained for 1 hour, so that the water and gas were completely removed, thereby avoiding inefficient QDs. After an hour, the vacuum system was closed, and nitrogen was passed through. The system was added with 0.1 mmol of Tris(trimethylsilyl) phosphine under nitrogen, and the temperature was increased to 260° C. for 20 minutes to obtain the InP core.

The temperature was then lowered to 230° C., and 0.22 mL of 1-dodecanethiol (DDT) was added for 1 hour. After an hour, 0.2 mmol of selenium was added to the mixture. Subsequently, 1 mL of n-trioctylphosphine was mixed and vortexed to a colorless liquid. Thereafter, it was warmed to 280° C. for 10 minutes, and then added with 4 mL of $Zn(OA)_2$. A total of 6.85 mL of ODE was mixed with 3.15 mL of oleic acid and then heated to 120° C. in a nitrogen atmosphere for 1 hour. It was then heated to 150° C. after 10 minutes and added with 0.55 mL of DDT. The temperature was increased to 300° C. for 90 minutes. The reaction was completed; cooled to room temperature; and mixed with 5 mL of QDs, 5 mL of hexane, and 20 mL of ethanol. The mixture was placed in a centrifuge tube and centrifuged four times at a rate of 7,800 rpm. After centrifugation, the resulting QD product was dissolved in hexane for storage.

After the end of the synthesis, the silica shell was coated, and the QDs were dispersed in water uniformly in order to allow the QDs to be dispersed in the aqueous solution. First, the magnet was placed into a single-necked flask; added with 0.3 mg/mL of QDs, 1 mL of CO520, and 9 mL of hexane; and placed in a drying oven at constant temperature and humidity. After an hour, TEOS was injected at a rate of 0.05 mL/h by using a microsyringe. After approximately an hour, 0.07 mL of ammonia water was added, stirred overnight, centrifuged at 12,000 rpm for 6 min, and washed three times. The InP@S QDs were dissolved in water for storage.

Conjugating InP@S QDs with RGP Peptide (InP-cRGD)

The aqueous solution (0.5 mL) of $NaYF_4$:Yb/Er@$NaYF_4$:Yb/Nd nanoparticles with a concentration of 10 mg/mL was added with 0.2 mL of MMP2-sensitive polypeptide (named MH-P08, with amino acid sequence of "SGAVRWLLTA"), 0.24 mL of NHS, and 0.024 mL of EDC to form UCNP-p. About 0.964 mL of the four compounds were mixed in an Eppendorf tube, stirred overnight, centrifuged three times with gravity at 12,000 rpm for 10 min, and stored in an aqueous solution. InP@S QDs were conjugated with the RGD tripeptide with chitosan to form InP@S-cRGD. First, 1 wt % chitosan was mixed with 2 wt % aqueous acetic acid solution. An aqueous solution of acetic acid with pH of 3.6 was neutralized with NaOH (200 mg) to increase the pH to 6. Subsequently, 100 mg of RGD was placed into 10 mL of aqueous solution and added with 0.3 mL of EDC and 0.3 mL of NHS. The mixture was kept in an ice bath for 15 minutes. An amount of 5.2 mL of chitosan acetic acid aqueous solution was added, and 0.5 mL RGD solution was obtained to stir with 0.2 mg/mL QDs overnight. The solution was centrifuged three times at 12000 rpm for 10 minutes and stored in a sample bottle. Lastly, 0.25 mL of UCNP-p solution with a concentration of 10 mg/mL was taken and conjugated with InP@S-cRGD solution with the same volume and concentration. The mixture was stirred for 2 hours and centrifuged three times at 12,000 rpm for 10 minutes. The final product, UCNP-p@InP-cRGD, was stored in an aqueous solution.

Synthesis of $NaYF_4$:Yb/Er@$NaYF_4$:Yb/Nd (UCNP)

UCNP was synthesized by high-temperature coprecipitation. Among the main materials of UCNP, the main lattice material with the best light-emitting efficiency was $NaYF_4$. The crystal phase of $NaYF_4$ was divided into cubic phase ($\alpha$-$NaYF_4$) and hexagonal phase ($\beta$-$NaYF_4$). UCNP of $\beta$ form was selected because of its high chemical stability, low phonon energy, and high light-emitting efficiency. $Y(CH_3CO_2)_3 \cdot H_2O$ (0.4 mmol), $Yb(CH_3CO_2)_3 \cdot H_2O$ (0.1 mmol), and $Er(CH_3CO_2)_3 \cdot H_2O$ (0.1 mmol) were dissolved in OA and ODE (3:7; 12.5 mL) at 150° C. under nitrogen for 30 minutes (Sigma, USA). The dissolved lanthanide salts were cooled down to 50° C. and stirred with methanol solution containing $NH_4F$ (2 mmol) and NaOH (1.25 mmol) for 30 minutes. Methanol was removed by heating the solution to 100° C. for 30 minutes. The solution was heated to 290° C. for 2 hours and cooled to room temperature. $NaYF_4$:Yb/Er nanoparticles were precipitated with absolute ethanol and recovered by centrifugation at 6000 rpm for 10 minutes. The prepared nanoparticles were stored in cyclohexane. The shell layer was synthesized using the same method, except that the Yb precursors were replaced with Nd to prepare a core-shell structure. The lanthanum acetate aqueous solution comprised 2.55 mL of $Er(CH_3CO_2)_3 \cdot H_2O$ (0.2 M), 0.17 mL of $Y(CH_3CO_2)_3 \cdot H_2O$ (0.2 M), and 0.68 mL of $Nd(CH_3CO_2)_3 \cdot H_2O$ (0.2 M). The section for synthesis was the same as the above. $NaYF_4$:Yb/Er@$NaYF_4$:Yb/Nd was obtained after centrifugation.

Conjugating $NaYF_4$:Yb/Er@$NaYF_4$:Yb/Nd with WP-2 Peptide (UCNP-p)

The aqueous solution (0.5 mL) of $NaYF_4$:Yb/Er@$NaYF_4$:Yb/Nd nanoparticles with a concentration of 10 mg/mL was added with 0.2 mL of MMP2-sensitive polypeptide (named MH-P08, with amino acid sequence of "SGAVRWLLTA"), 0.24 mL of NHS, and 0.024 mL of EDC to form UCNP-p. About 0.964 mL of the four compounds were mixed in an Eppendorf tube, stirred overnight, centrifuged three times with gravity at 12,000 rpm for 10 min, and stored in an aqueous solution.

Coupling UCNP-p with InP-cRGD (UCNP-p@InP-cRGD)

InP@S QDs were conjugated with the RGD tripeptide with chitosan to form InP@S-cRGD. First, 1 wt % chitosan was mixed with 2 wt % aqueous acetic acid solution. An aqueous solution of acetic acid with pH of 3.6 was neutralized with NaOH (200 mg) to increase the pH to 6. Subsequently, 100 mg of RGD was placed into 10 mL of aqueous solution and added with 0.3 mL of EDC and 0.3 mL of NHS. The mixture was kept in an ice bath for 15 minutes. An amount of 5.2 mL of chitosan acetic acid aqueous solution was added, and 0.5 mL RGD solution was obtained to stir with 0.2 mg/mL QDs overnight. The solution was centrifuged three times at 12000 rpm for 10 minutes and stored in a sample bottle. Lastly, 0.25 mL of UCNP-p solution with a concentration of 10 mg/mL was taken and conjugated with InP@S-cRGD solution with the same volume and concentration. The mixture was stirred for 2 hours and centrifuged three times at 12,000 rpm for 10 minutes. The final product, UCNP-p@InP-cRGD, was stored in an aqueous solution.

Example 1 Characterization of UCNP-p@InP-cRGD

The present UCNP-p@InP-cRGD was red fluorescence at 650-750 nm under 808 nm irradiation. Once entering into tumor cells, MMP-2 would digest the MMP-2 peptide thereby releasing InP-cRGD from UCNP. The cleaved UCNP-p@InP-cRGD converted the 808 nm irradiation into a green light with a wavelength of 520-540 nm.

Figure 4:
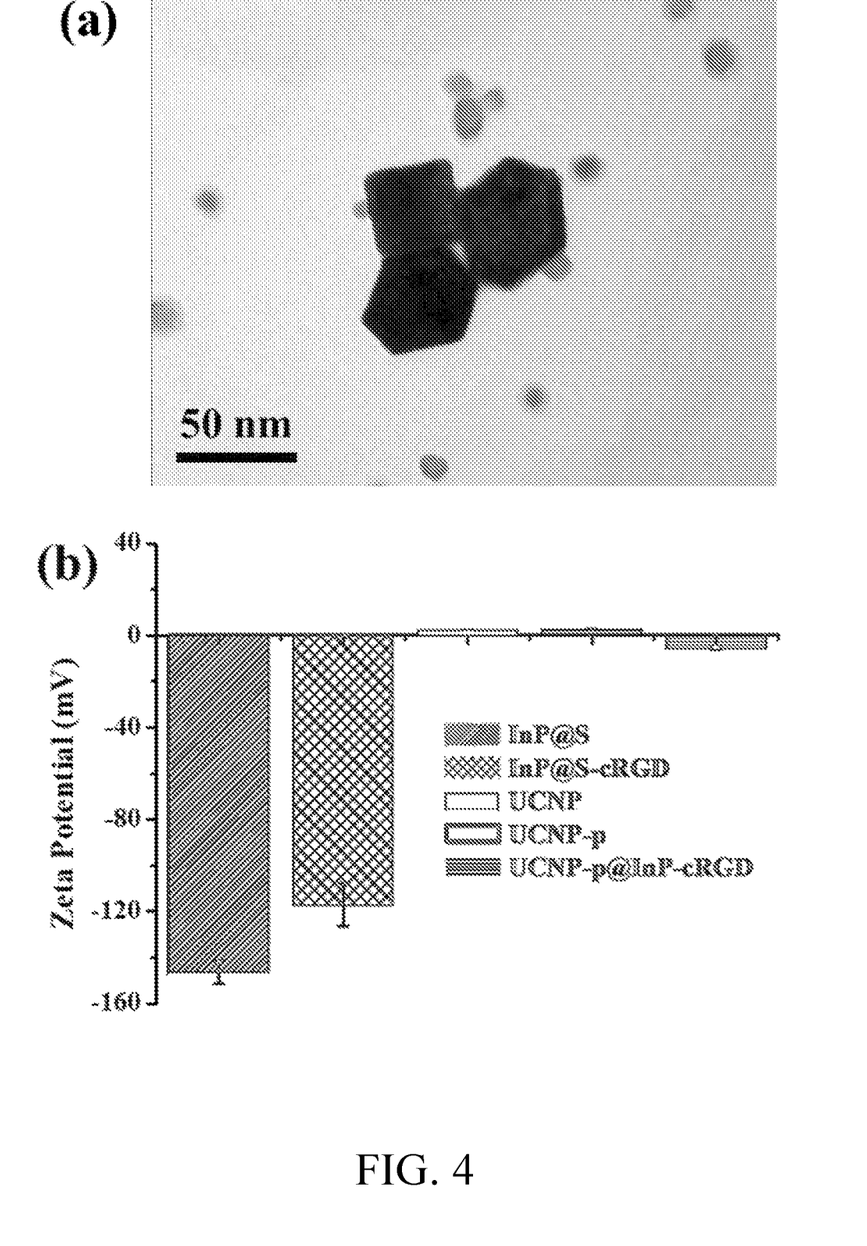
FIG. 4 is the data depicting the opto-electronic properties of the present nanocomposite according to Example 1 of the present disclosure. (a) The TEM image of UCNP-p@InP-cRGD. The scale bar represented 50 nm. (b) The potential of the nanocomposite was reached. (c) The size distribution of UCNP-p@InP-cRGD-modified MMP2. (d) Fourier-transform infrared spectroscopy (FTIR) spectra of QD modified QD complexes. InP@S: InP/ZnSeS/ZnS quantum dot coated with a silica shell; InP@S-cRGD: InP/ZnSeS/ZnS quantum dot coated with a silica shell, which has a RGD peptide coupled thereon; UCNP (upconversion nanoparticle): $NaYF_4$:Yb/Er@$NaYF_4$:Yb/Nd; UCNP-p: $NaYF_4$:Yb/Er@$NaYF_4$:Yb/Nd having an MMP-2-cleavable peptide coupled thereon; UCNP-p@InP-cRGD: UCNP-p coupled with InP@S-cRGD.

To further characterize the structure, UCNP-p@InP-cRGD was subjected to transmission electron microscopy (TEM), and the image was depicted in Panel (a) of FIG. 4. The electrophoretic mobility ($\mu_e$) of UCNP-p@InP-cRGD was determined by zeta potential (z) thereof. The data of Panel (b) of FIG. 4 indicated that the zeta potentials of UCNP, UCNP-p, and UCNP-p@InP-cRGD were obviously higher than that of InP@S and InP@S-cRGD. According to the analysis of dynamic light scattering (DLS), the UCNP-p@InP-cRGD had a particle size of about 100-475 nm (Panel (c) of FIG. 4). Regarding the infrared spectrum of UCNP-p@InP-cRGD, it was determined by FTIR, and the result was illustrated in Panel (d) of FIG. 4.

Figure 5:
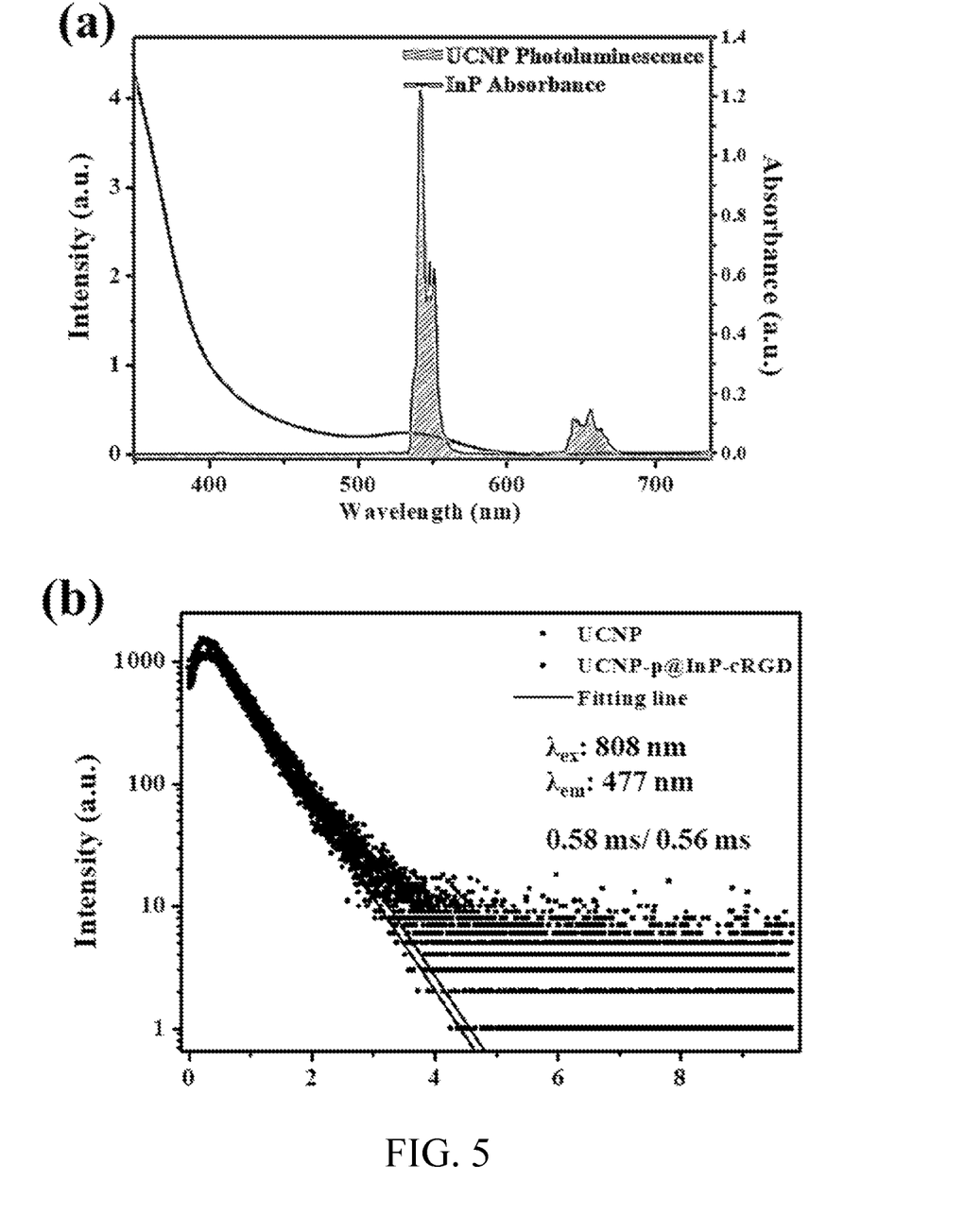
FIG. 5 is the data depicting the optical properties of the present nanocomposite according to Example 1 of the present disclosure. (a) Absorption and emission spectra of nanocomposites. (b) $NaYF_4$:Yb/Er@$NaYF_4$:YbNd and $NaYF_4$:Yb/Er@$NaYF_4$:Yb/Nd—InP QD fluorescence lifetime. (c) Fluorescence transfer between upconversion modification and nanocomposite. (d) Upconversion spectra and InP QD spectra with several human recombinant MMP2 proteins (rhMMP2). The concentration-dependent digestion of MMP2 was shown using photoluminescence spectrum, wherein 0.2 mg/mL of UCNP-p@InP-cRGD solution was incubated with 0, 20, 40, 60, 80, 100, or 120 pg/mL of rhMMP2 for 1 hour. UCNP: $NaYF_4$:Yb/Er@$NaYF_4$:Yb/Nd; InP: InP/ZnSeS/ZnS quantum dot; UCNP-p@InP-cRGD: UCNP coupled with InP, in which the UCNP has an MMP-2-cleavable peptide coupled thereon, and the InP is coated with a silica shell and has a RGD peptide coupled thereon.

The data of Panels (a)-(d) of FIG. 5 respectively illustrated that fluorescence process of UCNP-p@InP-cRGD of panel (a) of FIG. 2. Panel (a) of FIG. 5 showed the overlap between the fluorescence of UCNPs and the absorption peak of InP QDs and the phenomenon of fluorescence transfer between them. UCNP was identified as a fluorescent life cycle, and the change in its fluorescence lifetime after modification by the core-shell structure was observed. Panel (b) of FIG. 5 showed the nanocomposite of UCNPs combined with InP QDs. The lifetime was reduced from 0.58 ms to 0.56 ms because InP QDs absorb the upconverting fluorescence. As the characteristic peak of InP QDs absorbs the fluorescence of UCNPs, the fluorescence lifetime still has a tendency to decrease. For in vitro MMP2 sensing, human recombinant MMP2 (rhMMP2) was used for in vitro digestion of UCNP-p@InP-cRGD. The dose-dependent experiment of MMP2 digestion was performed that 20, 40, 60, 80, 100, and 120 pM rhMMP2 were added into 0.2 mg/mL UCNP-p@InP-cRGD for 37° C. incubation. The fluorescence intensity gradually increased with time (panel (c) of FIG. 5). Fluorescent emission at 540 nm demonstrated the performance of MMP2 in unraveling the UCNP-p@InP-cRGD. The exponential dose-dependent of MMP2-digested UCNP-p@InP-cRGD was between 80 pM to 100 pM. All enzyme reactions reached a plateau after 1 hour (panel (d) of FIG. 5).

Example 2 Bioactivity of UCNP-p@InP-cRGD

Figure 6:
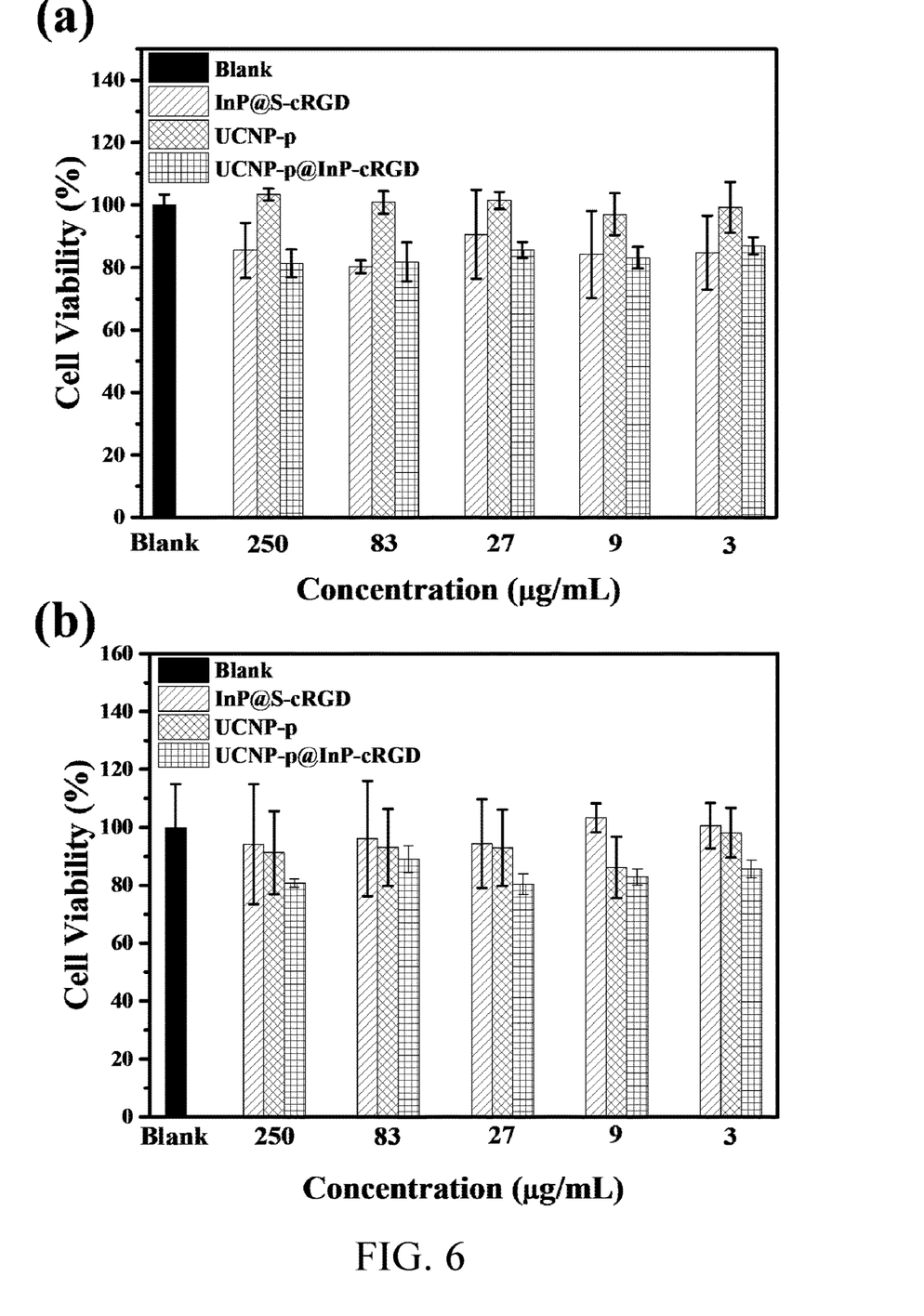
FIG. 6 is the data depicting the viability of cancer cells administered with specified treatments for 24 hour (a) or 48 hour (b) according to Example 2 of the present disclosure. InP@S-cRGD: InP/ZnSeS/ZnS quantum dot coated with a silica shell, which has a RGD peptide coupled thereon; UCNP-p: $NaYF_4$:Yb/Er@$NaYF_4$:Yb/Nd having an MMP-2-cleavable peptide coupled thereon; UCNP-p@InP-cRGD: UCNP-p coupled with InP@S-cRGD.

To evaluate the effect on cancer cells, UCNP-p@InP-cRGD was incubated with cancer cell line Ca922 (without MMP-2 expression) or HSC4 (with MMP-2 overexpsression) for 24 hours. The data of FIG. 6 suggested that the treatment of UCNP-p@InP-cRGD merely exhibited a marginal effect on cell viability.

Figure 7:
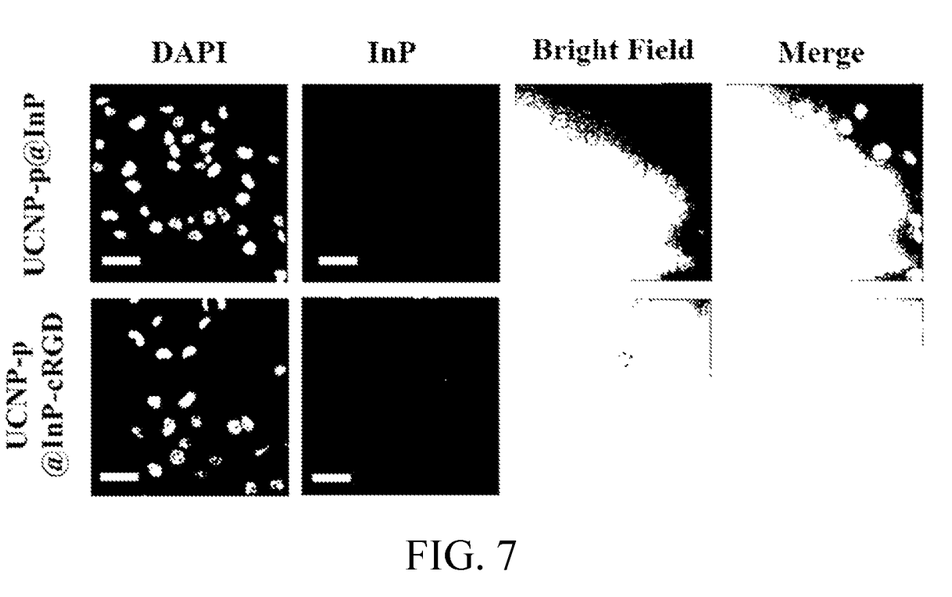
Figure 8:
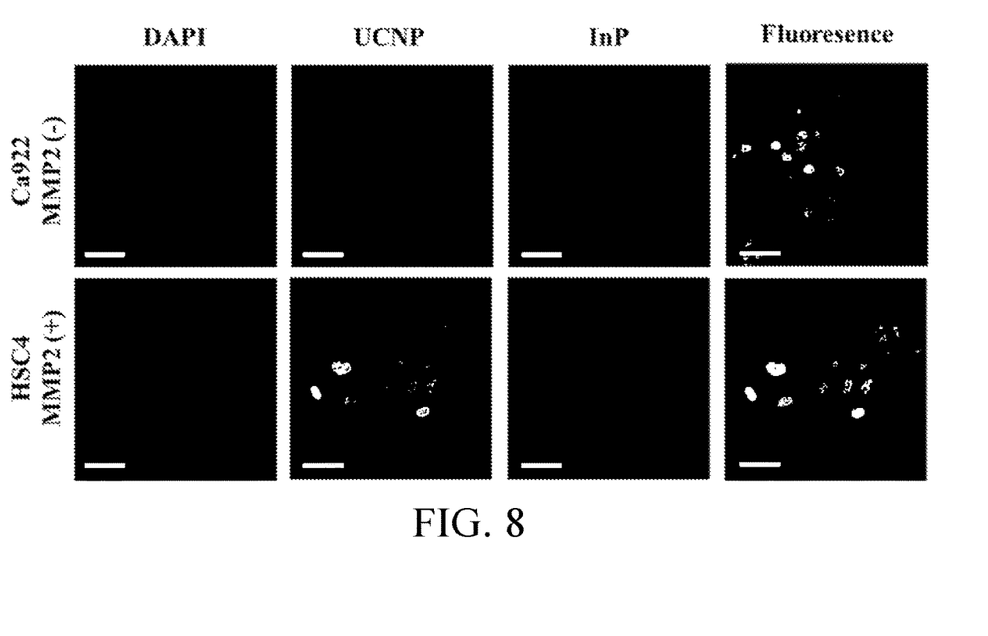
FIG. 8 is the data depicting the use of the present nanocomposite in detecting MMP-2 overexpressing cancer cells according to Example 2 of the present disclosure. Ca922 and HSC4 treated with UCNP-p@InP-cRGD for 12 hours. The treatments were processed by immunofluorescent staining and observed by fluorescence microscopy under 808 nm irradiation.

Compared with UCNP-p@InP, which did not have RGD peptide conjugated therewith, the present UCNP-p@InP-cRGD was effectively uptaken by cancer cells (FIG. 7). The data of FIG. 8 further confirms that the present UCNP-p@InP-cRGD was useful in distinguishing the cells with or without MMP-2 overexpression. Upon exposing with a 808 nm irradiation, the UCNP-p@InP-cRGD emitted a green light in HSC4 cells, while emitted a red light in Ca922 cells (FIG. 8).

Figure 9:
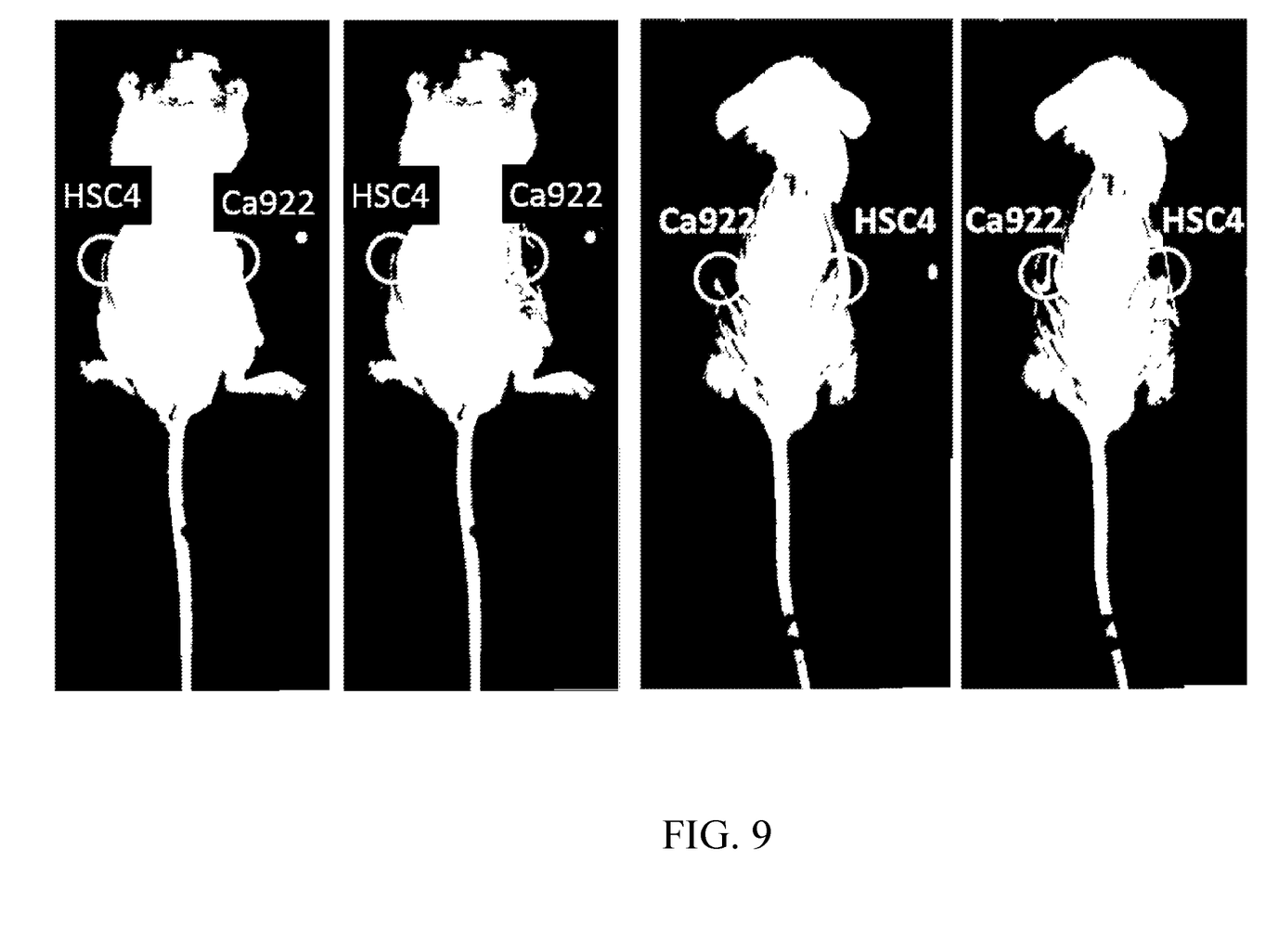

In addition to the in vitro study, the detecting effect of the present UCNP-p@InP-cRGD was also evaluated in animals, in which the Ca922 and HSC4 cells were respectively implanted subcutaneously in the left and right flanks of NOD scid gamma (NSG) mice. 21 days later, the present UCNP-p@InP-cRGD was intratumorally administered to the mice followed by exposing the mice with 808 nm irradiation. The emitting wavelength was measured, and the images were depicted in FIG. 9, in which the emitting wavelength of un-cleaved UCNP-p@InP (i.e., the UCNP-p@InP-cRGD in Ca922 cells) was predominantly detected under 600 nm channel, while the emitting wavelength of cleaved UCNP-p@InP (i.e., the UCNP-p@InP-cRGD in HSC4 cells) was predominantly detected under 535 nm channel.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A nanocomposite comprising,
a core-shell nanoparticle comprising,
    a phosphor core, which is made of a first phosphor material doped with one or more emitter ions;
    a shell layer encapsulating the phosphor core, wherein the shell layer is made of a second phosphor material doped with one or more absorber ions; and
    a cleavable peptide coupled to the shell layer; and
a core-shell quantum dot comprising,
    a center core, which is made of indium phosphide (InP), cadmium selenide (CdSe), cadmium selenide sulphide (CdSeS), zinc selenide (ZnSe), zinc cadmium selenide (ZnCdSe), or cadmium telluride (CdTe);
    an intermediate layer encapsulating the center core, wherein the intermediate layer is made of cadmium sulphide (CdS), cadmium zinc sulphide (CdZnS), or zinc selenide sulphide (ZnSeS);
    an outer layer encapsulating the intermediate layer, wherein the outer layer is made of zinc sulphide (ZnS);
    a silica layer encapsulating the outer layer; and
    an arginylglycylaspartic acid (RGD) peptide coupled to the silica layer;
wherein the core-shell nanoparticle is linked with the core-shell quantum dot via forming a peptide bond between the cleavable peptide and the RGD peptide.

2. The nanocomposite of claim 1, wherein the first and second phosphor materials are independently selected from the group consisting of, sodium yttrium fluoride, lanthanum fluoride, lanthanum oxysulfide, yttrium oxysulfide, yttrium fluoride, yttrium gallate, yttrium aluminum garnet, gadolinium fluoride, barium yttrium fluoride, and gadolinium oxysulfide.

3. The nanocomposite of claim 2, wherein each of the first and second phosphor materials is sodium yttrium fluoride.

4. The nanocomposite of claim 1, wherein the emitter ion and absorber ion are independently selected from the group consisting of, erbium (Er), ytterbium (Yb), thulium (Tm), holmium (Ho), neodymium (Nd), and praseodymium (Pr).

5. The nanocomposite of claim 4, wherein the first phosphor material is doped with Yb and Er, and the second phosphor material is doped with Yb and Nd.

6. The nanocomposite of claim 5, wherein the core-shell nanoparticle has a polygonal shape, in which each side of the polygon has an average length of about 20-35 nm.

7. The nanocomposite of claim 1, wherein the cleavable peptide is a peptide cleavable by matrix metallopeptidase (MMP), cathepsin, or plasminogen activator (PA).

8. The nanocomposite of claim 7, wherein the cleavable peptide is cleavable by MMP-2.

9. The nanocomposite of claim 1, wherein the center core is made of InP, and the intermediate layer is made of ZnSeS.

10. The nanocomposite of claim 9, wherein the core-shell quantum dot has a spherical shape, and an average diameter about 1-20 nm.

* * * * *